United States Patent [19]

Packard

[11] Patent Number: 4,913,259

[45] Date of Patent: Apr. 3, 1990

[54] COMPRESSIBLE EAR TIP

[75] Inventor: Thomas J. Packard, St. Paul, Minn.

[73] Assignee: Minnesota Mining and Manufacturing Company, St. Paul, Minn.

[21] Appl. No.: 357,779

[22] Filed: May 30, 1989

Related U.S. Application Data

[63] Continuation of Ser. No. 252,511, Sep. 30, 1988, Pat. No. 4,852,684, which is a continuation-in-part of Ser. No. 133,522, Dec. 16, 1987, abandoned.

[51] Int. Cl.$^4$ ................................................. A61B 7/02
[52] U.S. Cl. .................................... 181/131; 181/135; 128/864
[58] Field of Search ................. 181/131, 135, 137; 128/864–867

[56] References Cited

U.S. PATENT DOCUMENTS

| | | | |
|---|---|---|---|
| 3,303,902 | 2/1967 | Knott | 181/135 |
| 3,539,031 | 9/1968 | Scanlon | 181/129 |
| 3,618,600 | 4/1969 | Douglass | 128/864 |
| 3,768,470 | 10/1973 | Leight | 128/866 |
| 3,895,627 | 7/1975 | Leight | 128/865 |
| 3,896,801 | 7/1975 | Grout | 128/864 |
| 4,055,233 | 10/1977 | Huntress | 181/135 |
| 4,089,332 | 5/1978 | Rose | 128/865 |
| 4,261,432 | 4/1981 | Gunterman | 181/131 |
| 4,434,794 | 3/1984 | Leight | 128/867 |
| 4,552,137 | 11/1985 | Strauss | 128/864 |
| 4,564,009 | 1/1986 | Brinkhoff | 128/864 |

FOREIGN PATENT DOCUMENTS 2173110  10/1986  United Kingdom .

Primary Examiner—B. R. Fuller
Attorney, Agent, or Firm—Donald M. Sell; Walter N. Kirn; Robert W. Sprague

[57] ABSTRACT

An ear tip for use with a stethoscope, audio headset or like device, the ear tip being of a construction and design that provides substantial deformation of the ear tip under normal stethoscope pressures such that in use the ear tip is seated comfortably and conformably against the ear canal opening.

11 Claims, 1 Drawing Sheet

COMPRESSIBLE EAR TIP

CROSS REFERENCE TO RELATED APPLICATION

This application is continuation of copending application Ser. No. 07/252,511, filed Sept. 30, 1988, U.S. Pat. No. 4,852,684, which is a continuation-in-part of copending application Ser. No. 133,522, filed Dec. 16, 1987, abandoned.

BACKGROUND OF THE INVENTION

This invention relates to an ear tip for terminal attachment to a sound transmitting device such as a stethoscope, audio headset, acoustic speaker or the like.

Among the myriad devices employing ear tips, stethoscopes and audio headsets are among the most common. Both of these devices typically employ a spring-loaded means for forcing the ear tips into the user's ears in an attempt to create a sound-proof seal that maximizes the wearer's ability to hear only the desired sound free of ambient interference. This general design creates two related problems for the user. First, the exterior ear canal is rather sensitive to pressure and second, the ear canal varies in size and shape from person to person. Thus, hard conventional ear tips can cause serious discomfort by applying high pressure to the irregular surface of the user's ear canal. Furthermore, such hard ear tips form a poor acoustic seal with the ear, allowing ambient sound to infiltrate the ear canal and obscure the sound delivered by the device.

These problems of comfort and sound exclusion have been addressed in a number of ways, both as to ear tips and as to ear plugs. Soft, malleable materials such as air encased in a plastic bladder (U.S. Pat. Nos. 3,895,627, 3,768,470, and 4,089,332), a mushroom shaped soft rubber head (U.S. Pat. No. 3,618,600), malleable plastic (U.S. Pat. No. 4,552,137), and closed-cell foam encased in a plastic shell (U.S. Pat. No. 4,434,794) are described in the patent literature.

Design variations such as a flared, horn-shaped ear tip designed to fit over rather than into the ear canal (U.S. Pat. No. 3,303,902), various shapes with skirt-like flanges that insert into the ear canal (U.S. Pat. Nos. 4,564,009 and 3,896,801, G.B. patent No. 2,173,110 A), and soft mushroom-shaped ear tips (U.S. Pat. Nos. 4,055,233 and 3,539,031) have appeared as well. All such inventions rely upon pressure to create a good acoustic seal.

A further design, appearing in U.S. Pat. No. 4,552,137, teaches a solution where a tight fit is attained not by pressure but by a layer of adhesive on the ear tip's surface.

SUMMARY OF THE INVENTION

The present invention provides an ear tip adapted to deliver sound to a human ear, which ear tip comprises:
(a) a first section adapted to couple with a sound-transmitting device, and
(b) a second section connected to and in open communication with the first section, the second section comprising (1) walls defining a bulbous second section having a region of greatest outside diameter and a convex inner surface, which inner surface defines a hollow inner chamber, having an inside diameter and a length and (2) an outlet port adapted for open communication with the ear canal; wherein the second section presents a surface for contact with the ear;

the walls have a hardness in the range between (1) a lower limit above that hardness which will allow loss of open communication between the ear and the sound-transmitting device when the ear tip is in place in the ear, and (2) an upper limit of about 90 Shore A;

the second section is deformable under an axial force in the range between about 8 ounces and 12 ounces from a relaxed state to a compressed state, in which compressed state the ear-contacting surface is of substantially greater area than in the relaxed state; and the second section is adapted to conform in the compressed state to the external acoustic meatus of the ear.

The ear tip of the present invention is further characterized in one of several ways. In one aspect, the ear tip is characterized in that the greatest outside diameter of the second section is at least about 0.40 inches; and the ear tip exhibits a compression diameter increase of at least about 10% under an axial force of 12 ounces.

In another aspect, the ratio of (i) the length of the hollow inner chamber to (ii) the inside diameter of the second section measured in the region of greatest outside diameter of the second section is less than about 1.2; and the ear tip exhibits a compression distance factor of at least about 0.05 inches under an axial force of 8 ounces.

In yet another aspect, the second section has a maximum outside diameter of at least about 0.40 inches;

the ratio of (i) the inside diameter of the second section measured in the region of greatest outside diameter of the second section to (ii) the greatest outside diameter of the second section is between about 0.6 and about 0.95; and the ratio of (i) the length of the hollow inner chamber to (ii), the inside diameter of the second section measured in the region of greatest outside diameter of the second section is less than about 1.5.

In a final aspect, the ear tip of the present invention is characterized in that the walls have a minimum thickness in the region of greatest outside diameter of the second section and a greater thickness in the region nearer the outlet port, such that the ear tip bulges in the region of greatest outside diameter of the second section when the ear tip is subjected to an axial force in the range between about 8 ounces and 12 ounces.

The ear tip of the present invention includes two functional sections, a first section adapted for coupling to a sound-transmitting device, and a second section that further transmits such sound directly to the auditory canal via a chamber defined by the walls of the second section. The walls of the second section of the ear tip are preferably made of a solid or non-porous material rather than foamed elastomeric material. The walls are sufficiently flexible such that the second section will compress under the pressures conventionally exerted by spring-loaded stethoscopes and audio headsets. The surface area of the second section presented for occlusal contact with the external auditory canal is therefore substantially increased. A snug, comfortable, sound transmitting fit of the ear tip against the exterior of the auditory canal, particularly that anatomical portion known as the external acoustic meatus, is thus provided.

In particular embodiments, the walls of the second section of the ear tip are made of an elastomeric material that has a hardness factor within a range that will allow the second section to compress a substantial amount, on the order of 0.05 inches or greater, under the modest conventional pressures exerted by stethoscopes and audio headsets. The walls of this second section should present a smooth, compatible surface to the portions of the skin being contacted by the ear tip to avoid chemical and physical damage thereto. In a particular preferred embodiment, the walls forming the second section are designed to achieve an ear tip that bulges in a region interior of the terminal end of the second section, preferably by having walls that are thinnest in the interior region and become thicker from that region outwards to the terminus of the second section.

DESCRIPTION OF THE PREFERRED EMBODIMENTS

Figure 1:
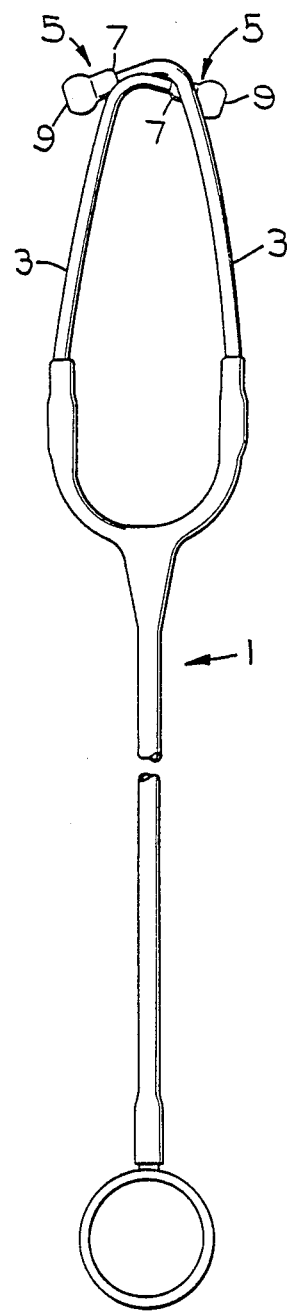
FIG. 1 is a plan view of a stethoscope equipped with ear tips of the present invention.

Referring to FIG. 1, a spring-loaded stethoscope 1 is shown having dual sound-transmitting tubes 3 each terminating in ear tips 5.

Figure 2:
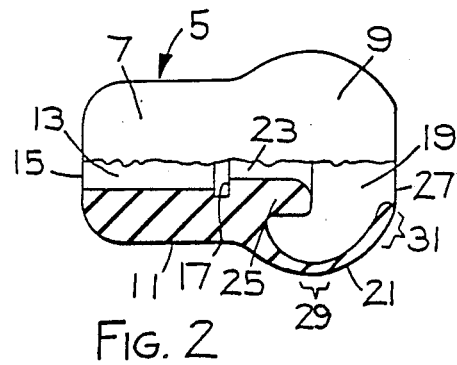
FIG. 2 is a plan view of the ear tip in the relaxed state with parts thereof broken away and shown in section.

The ear tip 5 of the present invention is shown in plan view in FIG. 2 in a relaxed or non-compressed state. Ear tip 5 is composed of two major sections, a first section 7 to which the tubes 3 (FIG. 1) are attached, and a second section 9 that serves as the terminus of stethoscope 1 in contact with the ear. Section 7 preferably has a generally cylindrical, symmetrical shape formed of first section walls 11 defining an axial extending central channel 13 adapted to receive tube 3 in frictional-fitting relationship. Interior of opening 15 of channel 13 are spaced-apart shoulders 17 that serve as a stop against which the end of tube 3 abuts.

Channel 13 communicates with hollow inner chamber 19 of second section 9 defined by second section walls 21. Second section walls 21 are relatively thin throughout, such that the ratio of (i) the inside diameter of the second section measured in the region of greatest outside diameter of the second section to (ii) the greatest outside diameter of the second section is between about 0.6 and 0.95, preferably between about 0.8 and 0.95. Second section walls 21 extend from junction with first section walls 11 outwardly for a distance and then inwardly thereafter with reference to the axis in a smooth, continuously curved, symmetrical fashion providing a generally bulbous second section with an inner surface that is convex relative to the inside of hollow inner chamber 19 and defines hollow inner chamber 19. Chamber 19 includes an entry port 23 defined by a short cylindrical stop 25 that projects into chamber 19 a predetermined distance to provide a stop means to prevent extensive inward compression of second section walls 21. Cylindrical stop 25 does not, however, project so far into chamber 19 that axial compression of the second section walls is totally prevented. Second section walls 21 terminate to define an outlet port 27 of circular cross-section for direct communication with the auditory canal. Port 27 is not integral with cylindrical stop 25, since such a construction would prevent the desired compression of the ear tip. To prevent occlusion of the port upon compression of the ear tip, port 27 has a diameter of at least about 0.1 inches (2.5 mm), preferably approximately 0.2 inches (5 mm).

As can be seen in the preferred embodiment of the ear tip shown in FIG. 2, the thickness of second section walls 21 varies from a minimum interior of the outlet port 27, generally in the region 29 of the greatest outside diameter of second section 9, to a maximum nearest the region 31 defining outlet port 27. The thickness of walls 21 preferably gradually increases from the minimum to the maximum. This construction permits the second section 9 to flex in the region 29 of minimum thickness under the pressures exerted by spring-loaded stethoscopes causing second section 9 to bulge outwardly, as shown in FIG. 3 to which reference is now made.

Figure 3:
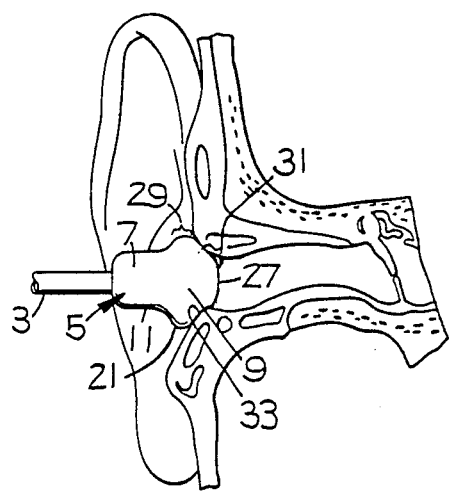
FIG. 3 is a plan view of the ear tip of FIG. 2 shown in its compressed state in the ear.

In FIG. 3, ear tip 5 is shown in its compressed state upon being forced against external acoustic meatus 33 of the human ear by pressure exerted through tube 3 of stethoscope 1. The ear tip does not penetrate deeply into the ear canal. Rather, the second section walls 21 flex in region 29 causing the walls to bulge, presenting a relatively large surface contact area to the external acoustic meatus. Spreading the force exerted by the stethoscope over a large area provides the enhanced comfort exhibited by the ear tip of the invention. Moreover, owing to the soft, elastic nature of the second section walls 21, the walls 21 are seen to conform closely to the irregular surface of the external acoustic meatus. The result is substantial exclusion of ambient noise, which along with comfort is a critical requirement for a stethoscopic ear tip.

To achieve the compression characteristics of the ear tip, the second section walls should be composed of a soft, elastic or elastomeric material that is preferably non-porous. Suitable materials include vulcanized natural rubber, vinyl elastomers, elastomeric polyurethanes, silicone rubbers, nitrile rubbers, and thermoplastic rubbers, such as are sold under the tradename Kraton G by the Shell Chemical Company. The second section walls 21 should also present a contact surface that is compatible with the area of the ear to which it will be exposed. Compatibility in this sense includes both resistance to the acidic oils present in the ear as well as low cytotoxicity.

While it is only the second section walls that need have the properties of compressibility and compatibility, as a practical matter it is preferred that the entire ear tip is constructed of a single material of the type described above. The ear tip may be fabricated by a variety of conventional methods including compression molding, transfer molding, liquid casting, and injection molding, particularly liquid injection molding. The latter is the preferred method due to its lower unit cost for large quantities.

The compressibility of the ear tips of this invention can be quantified in accordance with the following procedure. The ear tip under study is held on an ear tube in the moving pneumatic jaw element of an Instron force testing machine (Model 1122) using Instron Reversible load cell No. 2511-201. The speed of jaw movement (cross head speed) is 50 mm./min. The test is conducted at 25° C.

The machine is then set to cause the ear tip under study to be pressed against a rigid surface which is perpendicular to the axis of the ear tip and the direction of movement of the ear tip until a predetermined force is achieved (8 oz. (2.2 newtons) or 12 oz. (3.3 newtons), as appropriate). The testing machine reads out the axial displacement for each ear tip. Changes in outside diameter are determined by placing the ear tip on an ear tube and causing a flat, rigid surface perpendicular to the axis of the ear tip to be pressed against the ear tip with a static force (eight ounces or 12 ounces, as appropriate) parallel to the axis of the ear tip. The outside diameters prior to compression and while compressed are measured with an optical comparator.

Compression test data for two ear tips or the present invention are shown in Table I. Ear tips I and II had the configuration shown in FIG. 2. The thickness of second section wall 21 of ear tip I in region 29 is 0.015 in. (0.38 mm.) and gradually increases to 0.037 in. (0.94 mm.) in region 31. The thickness of second section wall 21 of ear tip II in region 29 is 0.015 in. (0.38 mm.) and gradually increases to 0.037 in. (0.94 mm.) in region 31. Ear tip I was composed entirely of REN:C:O-THANE polyurethane available from Ren Plastics Corp., product identification No. TDT-178-34 (undiluted). Ear tip II was composed entirely of a similar polyurethane available from the same source bearing a product identification number of RP 6401. Ear tip I had a Shore hardness value of 40 A; ear tip II had a Shore hardness of 70 A. The Shore hardness values are determined by ASTM D 2240-86 and values are read after 3 seconds.

Preferably, the ear tip of the present invention exhibits a compression distance factor of at least about 0.05 in. (1.3 mm.) under a compression force of 8 oz. (2.2 newtons). It is also preferred that the ear tip exhibits a compression diameter increase of at least about 7%, more preferably at least about 10%, under a compression force of 12 oz. (3.3 newtons). Under a compression force of 8 ounces, the ear tip preferably exhibits a compression diameter increase of at least about 0.02 inches, more preferably at least about 0.03 inches. Judicious matching of wall thicknesses, wall hardness and wall geometry yields a second section having the desired compression factors for the ear tip of the invention.

The force exerted by the stethoscope or other device, that is, the incoming force, is counterbalanced by a reactive force that can be resolved into two components, one parallel to the axis of the ear tips and one normal to that axis. The magnitude of those component forces depends upon disposition of the second section of the ear tip against the ear in the compressed state. The ear tip of the invention is constructed such that the reactive forces do not cause the ear tip to collapse or fold off its axis of symmetry; that is to say the ear tip is stable under conditions of use. This is accomplished by properly shaping the ear tip and by selecting materials of construction of the proper hardness.

As regards the shape of the ear tip, it is important that the ear tip not be necked down excessively such that the first section 7, or the area of interface between the first and second sections, has a much smaller outside diameter than does the second section in the region 29. Such a necking down may cause the ear tip, when placed in the ear under the force of a stethoscope or like sound-transmitting device, to fold over off its axis of symmetry, with concomitant loss of open communication between the ear and the sound-transmitting device. On the other hand, if the second section walls are not allowed to neck down somewhat between the region 29 and the first section, the second section walls will not bulge properly in region 29 and comfort to the user will be sacrificed.

Proper bulging and stability of the ear tip are affected by internal dimensions as well as by external dimensions, that is by the shape of the hollow chamber 19 as well as by the outside geometry of the ear tip. For present purposes, the dimensions of the hollow chamber 19 are (1) the greatest inside diameter, measured in region 29, and (2) the internal length, measured as the distance from the outside of the outlet port 27, past the region of greatest outside diameter, to the point where the cross-section of the hollow chamber is no longer decreasing. If the hollow chamber is too long relative to the greatest internal diameter, the stability of the ear tip will be sacrificed. For optimal performance, it is desirable for the ratio of internal length : greatest internal diameter to be less than 1.5, preferably less than 1.2, and most preferably less than 1.0. The presently preferred embodiment has a ratio of about 0.8.

As regards hardness, the harder the material, the thinner the wall should be in order for the ear tip to compress and spread properly under the load of the headset. The lower limit of Shore hardness is that which prevents the reactive forces from collapsing the second section in such a fashion that open communication between the first section and the ear canal is blocked. The geometry of the ear varies from individual to individual but as a practical matter a lower limit of about 10 A Shore hardness is suitable. On the upper end, a Shore hardness of about 90 A is considered suitable. At the present time, it appears that the preferred embodiment will be based on a hardness of 40 A to 50 A Shore hardness.

The wall thickness may typically vary from about 0.02 in. (0.5 mm.) to about 0.04 in. (1.0 mm.) in region 29 and about 0.04 in. (1.0 mm.) to about 0.08 in. (2.0 mm.) in region 31, most preferably about 0.03 in. (0.8 mm.) in region 29 and about 0.06 in. (1.5 mm.) in region 31. While walls of varying thickness as shown in FIG. 2 are preferred, uniform thickness walls of uniform thickness may be utilized, particularly at wall thicknesses in the thicker range of above about 0.05 in. (1.3 mm.).

While the ear tip is versatile as regards fitting in ears of various sizes and shapes, it may be desirable to vary the outside diameter to a degree in an effort to accommodate the very wide range of common ear canal sizes. The outside diameter of the ear tip in the region 29 is preferably at least about 0.40 inches to prevent penetration of the ear tip into the ear canal, and less than about 0.60 inches to assure that the ear tip will fit into the ear. The preferred maximum outside diameter in region 29 is about 0.48 inches.

It is recognized that stethoscopic ear tubes often comprise threaded ends adapted to engage a complementary threaded bore in an ear tip. The ear tip of the present invention can be made amenable to use with such ear tubes by inserting into first section 7 an adapter with the requisite threaded bore.

Further, it is recognized that alternative embodiments of the invention may be useful for applications other than stethoscopes. For example, first section 7 may be adapted to accept a small acoustic speaker. Thus, the invention provides an ear tip suitable for use with audio headsets.

TABLE I

| Ear Tip | Compression Force (oz.) | Compression Test Original Max. O.D. (in.) | Compression Test Compressed Max. O.D. (in.) | Increase in O.D.[a] | Compressed Dist.(in.)[b] |
|---|---|---|---|---|---|
| I | 8 (2.2N) | 0.53 (13.5 mm) | 0.65 (16.5 mm) | 22% (0.12 in; 3.0 mm) | 0.21 (5.4 mm) |
| II | 8 (2.2N) | 0.53 (13.5 mm) | 0.56 (14.2 mm) | 6% (0.03 in; 0.76 mm) | 0.077 (2.0 mm) |
| I | 12 (3.3N) | 0.53 (13.5 mm) | 0.66 (16.8 mm) | 24% (0.13 in; 3.3 mm) | |
| II | 12 (3.3N) | 0.53 (13.5 mm) | 0.61 (15.5 mm) | 15% (0.08 in; 2.0 mm) | |

[a] Referred to as the compression diameter increase.
[b] Referred to as the compression distance factor.

The claimed invention is:

1. A stethoscope having dual sound-transmitting tubes, each terminating in an ear tip adapted to deliver sound to a human ear, which ear tip comprises:
   (a) a first section adapted to couple with a sound-transmitting device, and
   (b) a second section connected to and in open communication with the first section, the second section comprising (1) walls defining a bulbous second section having a region of greatest outside diameter and a convex inner surface, which inner surface defines a hollow inner chamber having an inside diameter and a length, and (2) a outlet port adapted for open communication with the ear canal;
wherein
   the second section presents a surface for contact with the ear;
   the walls have a hardness in a range between (1) a lower limit above the hardness which will allow loss of open communication between the ear and the sound-transmitting device when the ear tip is in place in the ear, and (2) an upper limit of about 90 Shore A;
   the second section is deformable under an axial force in a range between about 8 ounces and 12 ounces from a relaxed state to a compressed state, in which compressed state the ear-contacting surface is of substantially greater area than in the relaxed state;
   the second section is adapted to conform in the compressed state to the external acoustic meatus of the ear;
   the greatest outside diameter of the second section is at least about 0.40 inches; and
   the ear tip exhibits a compression diameter increase of at least about 10% under an axial force of 12 ounces.

2. A stethoscope having dual sound-transmitting tubes, each terminating in an ear tip adapted to deliver sound to a human ear, which ear tip comprises:
   (a) a first section adapted to couple with a sound-transmitting device, and
   (b) a second section connected to and in open communication with the first section, the second section comprising (1) walls defining a bulbous second section having a region of greatest outside diameter and a convex inner surface, which inner surface defines a hollow inner chamber having an inside diameter and a length, and (2) a outlet port adapted for open communication with the ear canal;
wherein
   the second section presents a surface for contact with the ear;
   the walls have a hardness in a range between (1) a lower limit above that hardness which will allow loss of open communication between the ear and the sound-transmitting device when the ear tip is in place in the ear, and (2) an upper limit of about 90 Shore A;
   the second section is deformable under an axial force in a range between about 8 ounces and 12 ounces from a relaxed state to a compressed state, in which compressed state the ear-contacting surface is of substantially greater area than in the relaxed state;
   the second section is adapted to conform in the compressed state to the external acoustic meatus of the ear;
   a ratio of (i) the length of the hollow inner chamber to (ii) the inside diameter of the second section measured in the region of greatest outside diameter of the second section is less than about 1.2; and
   the ear tip exhibits a compression distance factor of at least about 0.05 inches under an axial force of 8 ounces.

3. A stethoscope having dual sound-transmitting tubes, each terminating in an ear tip adapted to deliver sound to a human ear, which ear tip comprises:
   (a) a first section adapted to couple with a sound-transmitting device, and
   (b) a second section connected to and in open communication with the first section, the second section comprising (1) walls defining a bulbous second section having a region of greatest outside diameter and a convex inner surface, which inner surface defines a hollow inner chamber having an inside diameter and a length, and (2) a outlet port adapted for open communication with the ear canal;
wherein
   the second section presents a surface for contact with the ear;
   the walls have a thickness in a range between (1) a lower limit above that hardness which will allow loss of open communication between the ear and the sound-transmitting device when the ear tip is in place in the ear, and (2) an upper limit of about 90 Shore A;
   the second section is deformable under an axial force in a range between about 8 ounces and 12 ounces from a relaxed state to a compressed state, in which compressed state the ear-contacting surface is of substantially greater area than in the relaxed state;
   the second section is adapted to conform in the compressed state to the external acoustic meatus of the ear;
   the second section has a maximum outside diameter of at least about 0.40 inches;
   a ratio of (i) the inside diameter of the second section measured in the region of greatest outside diameter of the second section to (ii) the greatest outside diameter of the second section is between about 0.6 and about 0.95; and
   a ratio of (i) the length of the hollow inner chamber to (ii) the inside diameter of the second section measured at the region of greatest outside diameter of the second section is less than about 1.5.

4. A stethoscope having dual sound-transmitting tubes, each terminating in an ear tip adapted to deliver sound to a human ear, which ear tip comprises:
   (a) a first section adapted to couple with a sound-transmitting device, and
   (b) a second section connected to and in open communication with the first section, the second section comprising (1) walls defining a bulbous second section having a region of greatest outside diameter and a convex inner surface, which inner surface defines a hollow inner chamber having an inside diameter and a length, and (2) a outlet port adapted for open communication with the ear canal;
wherein
   the second section presents a surface for contact with the ear;
   the walls have a hardness in a range between (1) a lower limit above that hardness which will allow loss of open communication between the ear and the sound-transmitting device when the ear tip is in place in the ear, and (2) an upper limit of about 90 Shore A;
   the second section is deformable under an axial force in a range between about 8 ounces and 12 ounces from a relaxed state to a compressed state, in which compressed state the ear-contacting surface is of substantially greater area than in the relaxed state;
   the second section is adapted to conform in the compressed state to the external acoustic meatus of the ear; and
   the walls have a minimum thickness in the region of greatest outside diameter of the second section and a greater thickness in a region nearer the outlet port, such that the ear tip bulges in the region of greatest outside diameter of the second section when the ear tip is subjected to an axial force in the range between about 8 ounces and 12 ounces.

5. A stethoscope according to any of claims 1–3, wherein the walls of the ear tip have a minimum thickness in the region of greatest outside diameter of the second section, and a greater thickness in a region nearer the outlet port such that the ear tip bulges in the region of greatest outside diameter of the second section when the ear tip is subjected to an axial force in the range between about 8 ounces and 12 ounces.

6. A stethoscope according to any of claims 1–4, wherein the second section walls of the ear tip have a lower limit of hardness of 10 on the Shore A scale.

7. A stethoscope according to any of claims 1–4, wherein the second section walls of the ear tip are polyurethane.

8. A stethoscope according to any of claims 1–4, wherein the second section walls of the ear tip are silicone.

9. A stethoscope according to any of claims 1–4, wherein the ear tip comprises a stop means projecting from the first section into the hollow inner chamber to limit the compression of the ear tip.

10. A stethoscope according to any of claims 1–4, wherein the ratio of (i) the inside diameter of the second section of the ear tip measured in the region of greatest outside diameter of the second section to (ii) the greatest outside diameter of the second section of the ear tip is between about 0.8 and about 0.95; and
   the ratio of (i) the length of the hollow inner chamber of the ear tip to (ii) the inside diameter of the second section of the ear tip measured in the region of greatest outside diameter of the second section of the ear tip is less than about 1.0.

11. A stethoscope according to any of claims 1–4, wherein the outlet port of the ear tip has a diameter of at least about 0.1 inches.

* * * * *

Disclaimer

4,913,259.—*Thomas J. Packard*, St. Paul, Minn. COMPRESSIBLE EAR TIP. Patent dated Apr. 3, 1990. Disclaimer filed Aug. 20, 1990, by the assignee, Minnesota Mining and Manufacturing Co.

The term of this patent subsequent to Aug. 1, 2006, has been disclaimed.
[ *Official Gazette Nov. 20, 1990* ]

UNITED STATES PATENT AND TRADEMARK OFFICE
CERTIFICATE OF CORRECTION

PATENT NO.  : 4,913,259
DATED       : April 3, 1990
INVENTOR(S) : Thomas J. Packard It is certified that error appears in the above-identified patent and that said Letters Patent is hereby corrected as shown below:

Col. 2, line 43, "(ii)," should be --(ii)--.

Col. 7, line 31, "the" should read --that--.

Signed and Sealed this

Twenty-seventh Day of August, 1991

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,913,259
DATED : April 3, 1990
INVENTOR(S) : Thomas J. Packard and Vern E. Radewald It is certified that error appears in the above-identified patent and that said Letters Patent is hereby corrected as shown below:

Col. 8, line 46, "thickness" should be --hardness--.

Signed and Sealed this

Thirteenth Day of July, 1993

Attest:

MICHAEL K. KIRK

Attesting Officer    Acting Commissioner of Patents and Trademarks